United States Patent
Vaidyanathan et al.

(10) Patent No.: US 9,188,583 B2
(45) Date of Patent: Nov. 17, 2015

(54) ECTOPARASITE DETECTION

(71) Applicant: SRI International, Menlo Park, CA (US)

(72) Inventors: Rajeev Vaidyanathan, Menlo Park, CA (US); Joseph Perrone, Harrisonburg, VA (US); Ellen Beaulieu, Menlo Park, CA (US); Scott Fields, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 14/382,113

(22) PCT Filed: Feb. 27, 2013

(86) PCT No.: PCT/US2013/028028
§ 371 (c)(1),
(2) Date: Aug. 29, 2014

(87) PCT Pub. No.: WO2013/130613
PCT Pub. Date: Sep. 6, 2013

(65) Prior Publication Data
US 2015/0064727 A1    Mar. 5, 2015

Related U.S. Application Data

(60) Provisional application No. 61/604,521, filed on Feb. 29, 2012, provisional application No. 61/624,324, filed on Apr. 15, 2012.

(51) Int. Cl.
| | |
|---|---|
| *G01N 33/53* | (2006.01) |
| *G01N 33/569* | (2006.01) |
| *A61K 35/12* | (2015.01) |
| *C07K 16/18* | (2006.01) |

(52) U.S. Cl.
CPC ............ *G01N 33/5308* (2013.01); *C07K 16/18* (2013.01); *G01N 2333/43552* (2013.01); *G01N 2333/43556* (2013.01); *G01N 2333/43582* (2013.01); *G01N 2333/43586* (2013.01)

(58) Field of Classification Search
CPC ..... A61K 35/64; A61K 39/395; G01N 33/53; G01N 33/569
USPC ................ 424/130.1, 520, 538; 435/7.1, 7.22
See application file for complete search history.

(56) References Cited

U.S. PATENT DOCUMENTS

| | | |
|---|---|---|
| 7,727,734 B1 | 6/2010 | Smith |
| 7,743,552 B2 | 6/2010 | Borth et al. |
| 8,460,890 B2 | 6/2013 | Smith |

FOREIGN PATENT DOCUMENTS

WO   WO 2013/130613 A1   9/2013

OTHER PUBLICATIONS

Arkle, S., et al., "Antibody Detection by ELISA in Chincken Infested with *Dermanyssus gallinae*," *Epidémil et santé anim* 48:15-19, Maison-Alfort, France (2005).

Blow, J.A., et al., "Stercorarial shedding and transtadial transmission of hepatitis B virus by common bed bugs (Hemiptera: Cimicidae)," *J Med Entomol* 38(5):694-700, The Entomological Society of America, United States (2001).

Eom, I.Y., et al., "Simultaneous sampling and analysis of indoor air infested with *Cimex lectularius* L. (Hemiptera: Cimicidae) by sold phase microextraction, thin film microextraction and needle trap device," *Anal Chim Acta* 716:2-10, Elsevier, Netherlands (February 2012)

Lowe, C.F. and Romney, M.G., "Bedbugs as vectors for drug-resistant bacteria,"*Emerg Infect Dis* 17(6):1132-1134, Centers for Disease Control and Prevention, United States (2011).

Mankin, R.W., et al., "Acoustic indicators for targeted detection of stored product and urban insect pests by inexpensive infrared, acoustic, and vibrational detection of movement," *J Econ Entomol* 103(5):1636-1646, Entomological Society of America, United States (2010).

Prudencio, C.R., et al., "Recombinant peptides as new immunogens for the control of the bovine tick, *Rhipicephalus (Boophilus) microplus*,"*Vet Parasitol* 172(1-2):122-131, Elsevier B.V., Netherlands (2010).

Szalanski, A.L., et al., "Multiplex polymerase chain reaction diagnostic of bed bug (HemipteraL Cimicidae)," *J Med Entomol* 28(4)937-940, Entomological Society of America, United States (2011).

International Search Report for International Patent Application No. PCT/US2013/028028, Korean Intellectual Property Office, Republic of Korea, mailed Jun. 3, 2013, 3 pages.

Written Opinon of the International Searching Authoriy for International Patent Application No. PCT/US2013/028028, Korean Intellectual Property Office, Republic of Korea, mailed Jun. 3, 2013, 5 pages.

*Primary Examiner* — Rodney P Swartz
(74) *Attorney, Agent, or Firm* — Sterne, Kessler, Goldstein & Fox, P.L.L.C.

(57) ABSTRACT

Ectoparasite infestation of a substrate like bedding is detected by contacting a sample from the substrate with a polyclonal ectoparasite antibody generated from a whole ectoparasite immunogen, under conditions wherein the antibody specifically binds ectoparasite antigen in the sample.

18 Claims, No Drawings

ECTOPARASITE DETECTION

FIELD OF THE INVENTION

The field of the invention is ectoparasite detection.

BACKGROUND OF THE INVENTION

Bloodsucking ectoparasites like bed bugs, fleas, lice, ticks and mites are not only health nuisances, but can be vectors for diseases like allergies (dust mites), epidemic typhus and epidemic relapsing fever (body lice), plague and murine typhus (certain fleas), Lyme disease, relapsing fever and many viral diseases (ticks), and scrub typhus (biting mites). The scale and the number of ectoparasite infestations in the United States have increased in the last ten years. For example, bed bugs are now commonly found in multi-unit housing such as apartments, dormitories, nursing homes, and hotels, and public venues such as theaters, public transportation, and shopping malls.

While bed bugs are not known vectors of any pathogen, there is some evidence that bed bugs could act as mechanical vectors of Hepatitis B virus (Blow et al. 2001). Methicillin-resistant *Staphylococcus aureus* (MRSA) and vancomycin-resistant *Enterococcus faecium* were recovered from bed bugs associated with a homeless shelter (Lowe et al. 2011).

The Second National Bed Bug Summit, 1-2 Feb. 2011, in Washington, D.C., concluded that detection is one of the most significant priorities in bed bug research. SRI International is developing a novel detection strategy to rapidly, conveniently, and unambiguously identify bed bug infestations at population densities lower than those normally detected by existing methods. Detection strategies currently in use include:

Visual detection: Personally checking mattresses and bedsprings, upholstery, and carpets for bed bugs, shed exoskeletons, or fecal droplets takes time and is often complicated by cryptic, inaccessible harborages;

Canine detection: Results with bed bug-sniffing dogs are highly variable. Success depends on the dog and trainer and type of entrainment and reward. Canine detection yields unacceptably high numbers of false positives, and its conspicuousness results in unpleasant public relations.

Active or passive monitors. Active monitors—such as Verifi® by FMC, CDC3000® by Stern Environmental, or NightWatch® by BioSensory, Inc.—rely on custom pheromone blends or carbon dioxide, to attract bed bugs to a trap. Passive monitors, such as the ClimbUp® Insect Interceptor, are placed near a sleeping person and use the heat and carbon dioxide of that person to attract and trap bed bugs. The efficacy of active and passive monitors depends on bed bug population density and may miss or underestimate small introductions of bugs. Most monitors also have an unacceptably large footprint, require specially trained personnel, and cost too much. In addition, both strategies involve actually handling dead bugs, which most people find unpleasant.

Other approaches to bed bug detection include:

Multiplex polymerase chain reaction (PCR) to distinguish bed bug eggs or leg fragments from human dwellings. This technique depends on physically recovering eggs or bug fragments and processing them using standard molecular biology reagents and techniques (Szalanski et al. 2011).

Microextraction of air samples to identify two well-characterized volatile pheromones, (E)-2-hexenal and (E)-2-octenal, by gas chromatography and mass spectrometry (Eom et al. 2012).

The use of infrared sensors, microphones, and a piezoelectric sensor to detect locomotion (Mankin et al. 2010).

Dow AgroSciences and Cytosignet, Inc., are developing antibody-based systems for bed bug detection; however, their systems use a limited number of bed bug-specific antigens. The Dow AgroScience system is based on detection of nitrophorin, a bed bug-specific salivary antigen, and the Cytosignet system depends on antigens specific to human blood voided in bed bug excreta.

We disclose a more robust polyclonal antibody detection kit for ectoparasites like bed bugs. In contrast to prior work, we have generated polyclonal antibodies against whole ectoparasites and lysates thereof such that our immunogen can include molecules from all nymphal instars, adult males, and adult females. Our invention is not only contrary to the teachings and conventions of the prior art, but was unexpected; for example, one skilled in the art would have expected cross-reactivity to present an impassable impediment, that negative-selection would not yield an effective residual species-specific antibody, that the hosts presented with the required immunogen would suffer impeding adverse local or systemic outcomes, e.g. infection, immunogenic shock, etc.

Our strategy provides a rapid, sensitive, discreet, and cost-effective procedure for early detection of ectoparasite infestation in both public and private dwellings. See also US20080148624 and US20100233731.

SUMMARY AND GENERAL DESCRIPTION OF THE INVENTION

The invention provides methods and compositions for detecting human ectoparasites, such as bed bugs, fleas, lice, ticks and mites.

In one aspect the invention provides methods of detecting ectoparasite infestation of a substrate, comprising: contacting a sample from the substrate with a polyclonal ectoparasite antibody generated from a whole ectoparasite immunogen, under conditions wherein the antibody specifically binds ectoparasite antigen in the sample; and detecting binding of the antibody and the antigen as an indication of ectoparasite infestation of the substrate.

In particular embodiments, the substrate is bedding, upholstery, or carpet material, and the method may further comprises the antecedent step of making the polyclonal ectoparasite antibody, comprising: immunizing an animal with a whole ectoparasite immunogen; and isolating from the animal resultant a polyclonal ectoparasite antibody.

In another aspect the invention provides methods of making a polyclonal ectoparasite antibody comprising: immunizing an animal with a whole ectoparasite immunogen; and isolating from the animal resultant a polyclonal ectoparasite antibody.

In particular embodiments, the immunogen comprises an extract of whole ectoparasites, preferably a combination of whole adult male and female ectoparasites, whole nymphs (multiple instars), and/or whole eggs. The extract may be a crude homogenate and/or lysate, optionally supplemented to improve immunogenicity, e.g. with a detergent, etc., and optionally clarified or filtered; however, to provide a robust antibody repertoire, the immunogen should be a whole ectoparasite immunogen and include diverse components representative of different portions of the whole ectoparasite's body, and preferably, different stages of the ectoparasites' life cycle, and/or both genders. In preferred embodiments the immunogen includes diverse components of entire cultures, including bodies, eggs and excretions and secretions, and the immunogens are not purified to remove particular ectoparasite or ectoparasite culture components.

The immunogen may be combined with an adjuvant to improve immunogenicity and/or antibody recovery, and routine immunization protocols may be used. The host can be any animal which generates a recoverable, responsive antibody. In particular embodiments, the host is a mammal, a non-human animal or mammal, or a conventional commercial antibody source, particularly a mammalian one, such as a horse, bovine, pig, goat, sheep, rabbit, rat, hamster, mouse, etc.

We have surprisingly found that mammalian hosts can tolerate immunogens of a variety of crude bed bug lysates and extracts, delivered with alternative adjuvants and immunization protocols, though care needs to be taken to adjust the dosage to the host to avoid harm or even death, e.g. by immunogenic shock; for example, 10-200 ug, or 20-100 ug, or 30 to 70 ug are typically operable for a rabbit, with about 50 ug proving ideal in some embodiments, whereas 5 ug is sufficient for a mouse. In any event, optimizing immunization dosages is routine in the art, and is practically guided by effective antibody production.

The method may further comprise the subsequent step of selecting the antibody against one or more non-ectoparasite antigens, such as other insect antigens, such as cockroach and dust mite antigens to improve ectoparasite specificity.

In another aspect the invention provides a polyclonal whole ectoparasite antibody, such as made by a subject method.

In another aspect the invention provides ectoparasite detection devices comprising: a polyclonal anti-whole-ectoparasite antibody; and a detection reagent for the antibody.

In particular embodiments, the ectoparasite antibody or the detection reagent comprises a direct or indirectly detectable label, and/or the device provides an ELISA format, such as a rapid immunodetection stick, like a home pregnancy test kit, such as wherein the anti-whole-ectoparasite antibody is conjugated to an enzyme and impregnated in a first zone of the stick and the reagent comprises an anti-ectoparasite antibody immobilized in a second zone of the stick, wherein at the second zone is impregnated a substrate of the enzyme.

The invention includes all combinations of particular embodiments as though each such combination was separately recited.

EXAMPLES

Polyclonal Antibodies against Whole Ectoparasite Lysates.

We homogenized nymphs, males, and females from a bed bug colony that has been maintained for almost 30 years. These samples were frozen and triturated in 1× phosphate buffered saline (PBS). We found these samples to be remarkably soluble even without the addition of any detergent. These lysates were clarified by 0.45 micron syringe filter, and protein concentration was determined by a standard Bradford protein assay. These clarified, quantified extracts were aliquoted into 1.5 mL Eppendorf tubes and stored at −80° C.

To generate polyclonal antibodies, we reconstituted bed bug extract in Freund's Complete Adjuvant (FCA) and 1×PBS. We vaccinated white New Zealand rabbits with the vaccine at 4 separate subcutaneous locations. Booster injections of the vaccine reconstituted in Freund's Incomplete Adjuvant (FIA) were administered at 2-week intervals for 8 weeks. Serum samples were collected on Day 1 and on each day of the booster injections for enzyme linked immunosorbent assay (ELISA) analysis. On day 70, the rabbits were exsanguinated and total serum was harvested, pooled, aliquoted and stored at −80° C.

The individual bleeds and pooled serum were assayed by ELISA. Individual wells of a 96-well plate were coated overnight with 100 µl of bed bug lysate diluted to 2 µg/mL in PBS or PBS with no lysate. Two-fold dilutions (starting at a 1:1000 dilution) of the serum harvested at each day or the pooled serum were added to the indicated wells for 1 hr at room temperature. The plates were washed, and detection was conducted using an anti-rabbit IgG mouse monoclonal antibody conjugated to horseradish peroxidase. Following the addition of detection substrate and stop solution, the plates were photographed and scanned in a microplate reader. We generated a strong antibody response to the bed bug lysate, and the pooled serum revealed a titer of greater than a 1:150,000 dilution.

The same protocol is used to generate polyclonal antibodies against alternative human ectoparasites including fleas, lice, ticks and mites.

Determination of Ectoparasite Antisera Specificity.

We produced lysates of the house dust mite *Dermatophagoides farinae*, the German cockroach *Blatella germanica*, and the American cockroach *Periplaneta americana*. We used the same buffer and protocol as those for bed bugs. These extracts were analyzed by ELISA to determine the degree of cross-reactivity of our antibodies. We generated a cross-adsorption affinity column to remove antibodies generated by this first pass that cross-react with other arthropod antigens and are, therefore, not specific to bed bugs.

At titers of 1:60,000 (rabbit 1) and 1:50,000 (rabbit 2), our reagent is highly specific for bed bugs. We detected no cross-reactivity with lysates of house dust mites (DM, *Dermatophagoides farina*), German cockroach (GC, *Blatella germanica*) or American cockroach (AC, *Periplaneta americana*).

We have generated the antibodies and reagents necessary and sufficient to incorporate into a point-of-use assay to detect antigens specific to bed bugs. Such assay products can utilize a sandwich, well, or lateral flow immunochromatographic "stick" design. The end-user can swab or wipe in target areas, such as behind headboards or under a mattress, and insert the sample into the reader. Optional reagents can include a solution to solubilize bed bug-specific antigens from the collection device. In particular embodiments, the solution will migrate over a region with immobilized antibodies conjugated to a detection agent. The final assay can utilize visual, colorimetric, fluorescent, or luminescent detection modalities.

The same methods are used to confirm specificity of the polyclonal antibodies against alternative human ectoparasites including fleas, lice, ticks and mites.

REFERENCES

Blow J A, Turell M J, Silverman A L, Walker E D. 2001. Stercorarial shedding and transtadial transmission of hepatitis B virus by common bed bugs (Hemiptera: Cimicidae). J Med Entomol 38: 694-700.

Eom I Y, Risticevic S, Pawliszyn J. 2012. Simultaneous sampling and analysis of indoor air infested with *Cimex lectularius* (Hemiptera: Cimicidae) by solid phase microextraction, thin film microextraction and needle trap device. Anal Chim Acta 716: 2-10.

Lowe C F, Romney M G. 2011. Bedbugs as vectors for drug-resistant bacteria. Emerg Infect Dis 17: 1132-1134.

Mankin R W, Hodges R D, Nagle H T, Schal C, Pereira R M, Koehler P G. 2010. Acoustic indicators for targeted detection of stored product and urban insect pests by inexpensive infrared, acoustic, and vibrational detection . . . . J Econ Entomol 103: 1636-1646.

Szalanski A L, Tripodi A D, Austin J W. 2011. Multiplex polymerase chain reaction diagnostics of bed bug (Hemiptera: Cimicidae). J Med Entomol 48: 937-940.

The descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of detecting a human ectoparasite infestation of a dwelling substrate, comprising:
   contacting a sample from the substrate with a polyclonal antibody generated from an immunogen comprising an extract of a whole ectoparasite, under conditions wherein the antibody specifically binds an antigen of the ectoparasite in the sample;
   detecting binding of the antibody and the antigen as an indication of infestation of the substrate with the ectoparasite.

2. The method of claim 1 wherein the ectoparasite is selected from bed bugs, fleas, lice, ticks and mites.

3. The method of claim 1 wherein the ectoparasite is bed bugs.

4. The method of claim 1 wherein the substrate is bedding, upholstery, or carpet material.

5. The method of claim 1 further comprising making the polyclonal antibody comprising:
   immunizing an animal with the ectoparasite immunogen; and
   isolating from the animal the resultant polyclonal anti-ectoparasite antibody.

6. A method of making a polyclonal ectoparasite antibody comprising:
   immunizing an animal with an immunogen comprising an extract of a whole ectoparasite; and
   isolating from the animal a resultant polyclonal anti-ectoparasite antibody.

7. The method of claim 6 wherein the ectoparasite is selected from bed bugs, fleas, lice, ticks and mites.

8. The method of claim 6 wherein the ectoparasite is bed bugs.

9. The method of claim 6 wherein the extract of the whole ectoparasite is an extract of a combination of whole adult male and female ectoparasites, whole nymphs, and whole eggs.

10. The method of claim 6 further comprising removing non-ectoparasite antibodies against one or more non-ectoparasite antigens.

11. The method of claim 6 wherein the animal is a rabbit, and the immunogen is about 50 μg.

12. A polyclonal anti-ectoparasite antibody made by the method of claim 6, 7 or 8.

13. An ectoparasite detection device comprising:
    a polyclonal anti-whole-ectoparasite antibody; and
    a detection reagent for the antibody.

14. The device of claim 13 wherein the ectoparasite is selected from bed bugs, fleas, lice, ticks and mites.

15. The device of claim 13 wherein the ectoparasite is bed bugs.

16. The device of claim 13 wherein the anti-ectoparasite antibody or the detection reagent comprises a direct or indirectly detectable label.

17. The device of claim 13 in a portable, lateral flow immunochromatographic design format.

18. The device of claim 13 provided as an ELISA-based rapid immunodetection stick, wherein the anti-whole-ectoparasite antibody is conjugated to an enzyme and impregnated in a first zone of the stick and the reagent comprises an anti-ectoparasite antibody immobilized in a second zone of the stick, wherein at the second zone is impregnated a substrate of the enzyme.

* * * * *